United States Patent [19]

Mauchien et al.

[11] Patent Number: 5,627,641

[45] Date of Patent: May 6, 1997

[54] ISOTOPIC ANALYSIS PROCESS BY OPTICAL EMISSION SPECTROMETRY ON LASER-PRODUCED PLASMA

[75] Inventors: Patrick Mauchien, Palaiseau, France; Walter Pietsch, Graz, Austria; Alain Petit; Alain Briand, both of Paris, France

[73] Assignee: Commissariat a l'Energie Atomique, Paris, France

[21] Appl. No.: 381,991

[22] PCT Filed: Jun. 14, 1994

[86] PCT No.: PCT/FR94/00708

§ 371 Date: Jun. 14, 1995

§ 102(e) Date: Jun. 14, 1995

[87] PCT Pub. No.: WO94/29699

PCT Pub. Date: Dec. 22, 1994

[30] Foreign Application Priority Data

Jun. 15, 1993 [FR] France .................................. 93 07179

[51] Int. Cl.[6] .................................................. G01N 21/63
[52] U.S. Cl. .................................................. 356/318
[58] Field of Search .................................... 356/318, 317

[56] References Cited

U.S. PATENT DOCUMENTS 4,794,230 12/1988 Seliskar et al.
5,133,901 7/1992 Peterson et al. .......................... 209/3.2

FOREIGN PATENT DOCUMENTS 1024687 2/1965 United Kingdom.

OTHER PUBLICATIONS

Watcher et al, Applied Spectroscopy, vol. 41, No. 6, 1987, pp. 1042–1048.

Patent Abstracts of Japan –Janvier 1988 –vol. 12, No. 224 (P–721 (3071) 25 Jun. 1988 & JP–A–63 018 249 (Kawasaki Steel Corp) 26.

Determination of Uranium Isotopes in a Complex Matrix by Optical Spectroscopy –G.M. Murray et al., –Journal of Alloys and Compounds –vol. 181, 1992 –pp. 57–62.

*Primary Examiner*—F. L. Evans
*Attorney, Agent, or Firm*—Burns, Doane, Swecker & Mathis, LLP

[57] ABSTRACT

Isotopic analysis process by optical emission spectrometry on laser-produced plasma. According to the invention, the sample to be analyzed (10) is irradiated by a laser beam (20) to produce a plasma (13), the light spectrum emitted by said plasma is analyzed and from it is deduced the isotopic composition of the sample. Application to isotopic analysis in the nuclear industry.

3 Claims, 2 Drawing Sheets

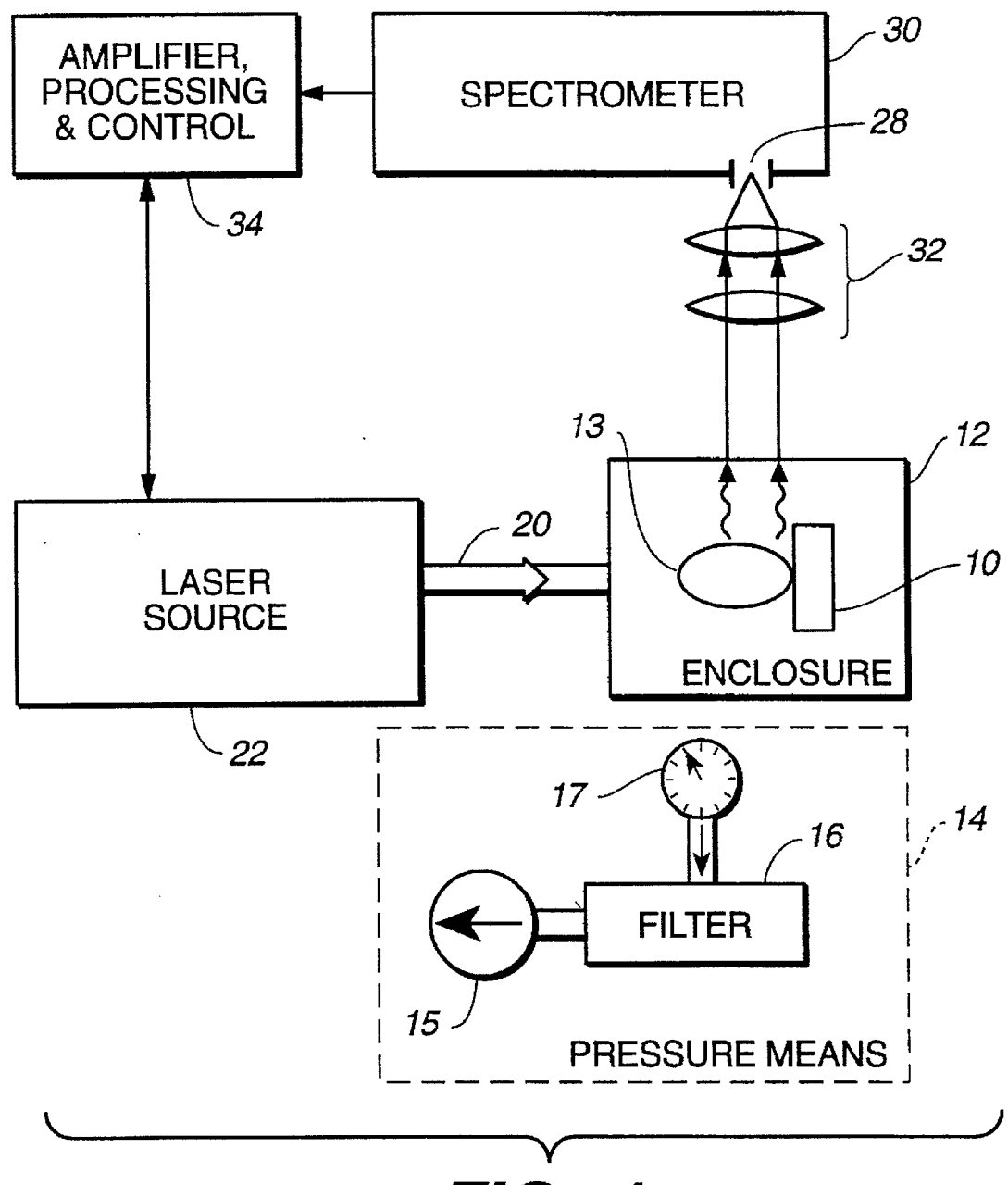
FIG._1

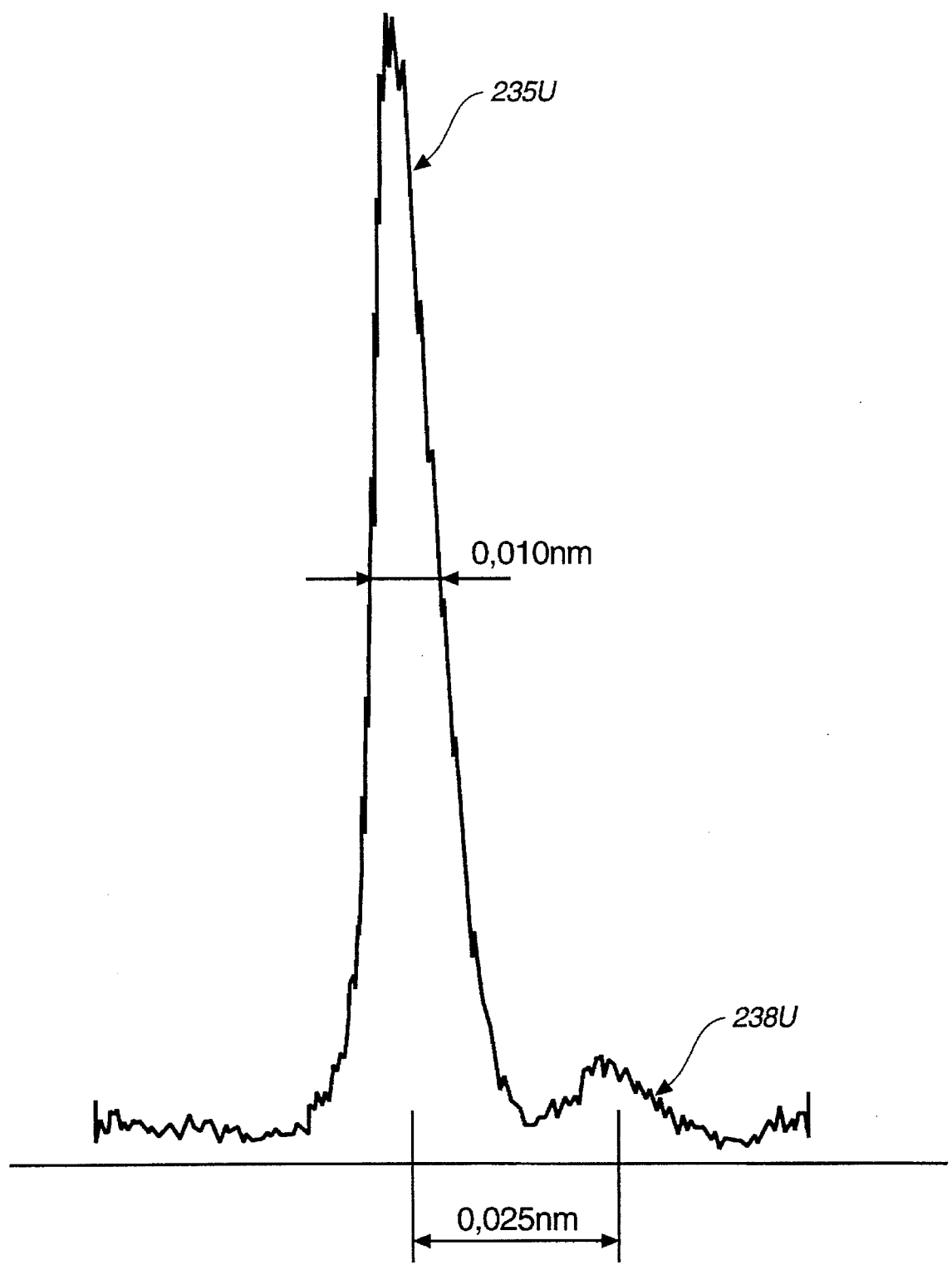
FIG._2

ISOTOPIC ANALYSIS PROCESS BY OPTICAL EMISSION SPECTROMETRY ON LASER-PRODUCED PLASMA

DESCRIPTION

TECHNICAL FIELD

The present invention relates to an isotopic analysis process by optical emission spectrometry on a laser-produced plasma.

It is used in the measurement of the isotopic concentrations of elements. One of the preferred fields of the invention is the nuclear industry.

PRIOR ART

Measurements of isotopic concentrations of elements are generally performed by mass spectrometry. The sample to be analyzed is dissolved, then atomized and then thermally ionized. The ions are then separated in accordance with their mass before being counted.

Mass spectrometry is characterized by a very good sensitivity and an excellent precision of the measurements. However, apart from the fact that it requires preparative chemistry for dissolving the samples, it involves the use of sophisticated and expensive equipment, which can only be used in the laboratory.

Another procedure for measuring isotopic concentrations consists of the spectral analysis of the emission radiation of a source of excited atoms. In this case, separation takes place with the aid of a spectrometer, of the emission wavelengths, which can differ very significantly for several isotopes of the same element (isotopic shift effect). The measurement of the isotopic concentrations is then obtained by measuring the emission signal corresponding to each isotope.

Optical emission spectrometry on high frequency-induced plasma (or OES/HFIP for short) uses this principle and has e.g. been used for the isotopic analysis of uranium. This procedure is fast and relatively economic. However, it is not very precise and, like mass spectrometry, it cannot be envisaged for use outside the laboratory.

Alpha counting spectrometry can also be considered for radio-active elements, because it is not very onerous and is relatively simple to perform. It can also be used for the direct analysis of solid samples. However, its field of use is very restricted. The alpha particles detected are those which emit the surface atomic layers, the others being absorbed in the sample. This means that the measurement is only representative of the sample surface. Mass analysis consequently requires a preparative chemistry (dissolving the sample and preparing deposits of very small thickness).

Another limiting factor is linked with the radioactive material concentration. For example, in the case of uranium, if the concentration is too high (a few $mg/cm^2$), interferences occur (overlap of the corresponding peaks of $U_{234}$, $U_{235}$ and $U_{238}$). For low concentrations, the counting times are very long (several minutes and even several dozen minutes). In the best of cases, the precision level of alpha spectrometry for isotopic analysis is a few per cent.

Gamma counting spectrometry has promising performance characteristics for the isotopic analysis of uranium. It is a non-destructive analysis process, which also offers the possibility of a direct determination of the uranium mass. However, the counting and therefore analysis times are very long. It only relates to radioactive elements and does not permit a precise cartography of the isotopic composition of the samples. Finally, it cannot be envisaged as an in situ analysis method.

A spectral analysis process is also known, which consists of irradiating a sample by a pulse laser beam in order to produce a plasma, analyzing the spectrum of the light emitted by said plasma and deducing from said spectrum the elementary composition of the sample.

By analogy with the usual terminology in the field, this process can be called optical emission spectrometry on laser-produced plasma or OES/LPP for short. Such a process is e.g. described in GB-A-1,024,687.

This process is e.g. used for copper, stainless steel, molybdenum, tungsten and graphite. It is suitable for determining the elementary composition of the sample, but a priori does not make it possible to carry out an isotopic analysis which requires a much greater analysis precision. Thus, the isotopic shifts are generally smaller than the spectral shifts corresponding to different elements. If e.g. the OES/LPP method is applied to uranium, which has a relatively high isotopic shift of approximately 0.025 nm and using a power density of 1.4 $GW/cm^2$ for a pulse time of 28 ns, which represents an energy of 30 milliJoules, there is a mid-height line width of 0.07 nm, which is approximately three times the isotopic shift. Therefore this process would appear to be unsuitable for isotopic analysis.

DESCRIPTION OF THE INVENTION

The present invention is directed at an OES/LPP-type process, but whose experimental conditions are such that isotopic analysis becomes possible.

The first condition to be fulfilled is that each pulse of the laser beam has an energy below a few $milliJoules/cm^2$, e.g. below 10 $mJ/cm^2$.

Preferably, a second condition should be satisfied. It must be possible to carry out the spectral analysis with a certain time lag compared with the laser pulse, said lag being at least 200 ns.

Preferably, the analysis of the light emitted by the spectrum must relate to a plasma volume at a certain distance from the surface of the sample, which is at least 0.5 mm.

The invention can apply to elements having a high isotopic shift, particularly uranium and plutonium, but also to rare earths (Nd, Sm, Gd, Er) or tungsten.

BRIEF DESCRIPTION OF THE DRAWINGS

FIG. 1 is a basic diagram of equipment performing the process according to the invention.

FIG. 2 is an OES/LPP spectrum obtained on enriched uranium.

DETAILED DESCRIPTION OF AN EMBODIMENT

The diagram of equipment performing the invention is given in FIG. 1. The sample to be analyzed 10 is placed in an enclosure 12 in which the pressure is maintained at a few dozen mtorr with the aid of conventional means 14 (pump 15, filter 16, pressure measuring device 17, etc.). A laser beam 20 is directed onto the sample and is produced by a laser source 22. This laser can be of type XeCl or Nd:YAG or of any other type. It preferably operates in pulse-like manner.

The energy deposited on the sample 10 by the laser beam (a few $mJ/cm^2$, e.g. 10 $mJ/cm^2$) leads to the tearing away of material and the formation of a light plasma 13. Part of the light emitted by a precise volume fraction of the plasma 13 is collected and focussed onto the entrance slit 28 of a spectrometer 30 having a high spectral resolution by a simple optical system 32 using the combination of several lenses and/or one or more not shown fibres. The spectrometer 30 makes it possible to separate the different radiations from the plasma. The light signal is collected on one or more photomultipliers, or on a multichannel detector. An amplification, signal processing and control cascade is associated with the spectrometer 30 and the laser 22.

As stated hereinbefore, certain experimental conditions must be respected in order to obtain emission line widths compatible with an isotopic analysis. It is necessary to master a certain number of experimental parameters such as the laser energy for irradiating the samples and the measurement space-time conditions. The laser energy must not exceed a few mg/cm$^2$ and must be in pulse form (e.g. less than 10 mJ/cm$^2$), because beyond this the plasma is too dense and hot and the emission lines widen considerably. The emission signal must be collected in a volume at a distance from the sample surface of at least 0.5 mm. The time lag between the laser pulse and the time of the measurement must be at least 200 ns.

FIG. 2 shows an example of the result obtained with an enriched metallic uranium sample (93.5% $U_{235}$, 5.3% $U_{238}$ and 1.2% $U_{234}$). The plasma was produced by a XeCl laser focussed on a microregion. The spectrum represents the recording of the emission signal of the plasma on a spectral range of 0.085 nm around the atomic transition at 424.4372 nm of the uranium ion. The intense peak (mid-height width of 0.01 nm) is due to the emission of the isotope $U_{235}$. To the right of the $U_{235}$ peak, there is a second, less intense peak, corresponding to $U_{238}$ emission. The spectral shift between the two peaks is 0.025 nm, which is in accordance with the known isotopic shift for said line.

By measuring the respective intensities of the two peaks (or their surface), it is easy to determine the relative abundances of the two isotopes. In the embodiment used here, an intensity ratio of $U_{235} \cdot U_{238}$ is 16.7, whereas the true concentration ratio is 17.64 (93.5%:5.3%). This ratio of 16.7 leads to an error of 5% on the determination of the concentration of $U_{238}$ (5.6% instead of 5.3%) and 0.3% on the determination of $U_{235}$ (93.2% instead of 93.5%).

These results can be considerably improved on the one hand by increasing the number of measurements and on the other by simultaneously performing the measurements on the two peaks $U_{238}$ and $U_{235}$. This makes it possible to achieve a precision level better than 1% for $U_{238}$. By using uranium standards, it is also simple to determine absolute abundances.

These results clearly show the feasibility of the invention for the isotopic analysis of $U_{235}$ and $U_{238}$. However, on the spectrum there is no peak corresponding to the emission of $U_{234}$. This is due to its low density (1.2% concentration) and the fact that it is probably not clearly separated from the $U_{235}$ peak.

We claim:

1. A process for isotropic analysis of a sample comprising the steps of:

irradiating said sample to be analyzed by a pulse-type laser beam to produce a plasma on its surface, said plasma emitting a spectrum of light, and said each pulse of said laser beam having an energy equal to or below ten milliJoules per cm$^2$;

analyzing said spectrum of the light at a time lag of at least equal to 200 ns relative to said laser pulse, wherein isotropic information is obtainable to allow said isotropic analysis.

2. The process according to claim 1, wherein analyzing said spectrum of said light relates to a plasma volume located a distance from said sample surface of at least 0.5 mm.

3. The process according to claim 1, wherein said sample is of uranium or plutonium.

* * * * *

UNITED STATES PATENT AND TRADEMARK OFFICE

CERTIFICATE OF CORRECTION

PATENT NO. : 5,627,641

DATED : May 6, 1997

INVENTOR(S) : Patrick Mauchien, Walter Pietsch, Alain Petit, Alain Briand

It is certified that an error appears in the above-identified patent and that said Letters Patent is hereby corrected as shown below:

On the title page:

Item [73]: Assignee, after "Paris, France" insert --and Compagnie Generale Des Matieres Nucleaires, Velizy-Villacoublay Cedex, France.--

Signed and Sealed this

Twenty-fourth Day of March, 1998

Attest:

BRUCE LEHMAN

*Attesting Officer*     *Commissioner of Patents and Trademarks*